United States Patent [19]

Nuzzo

[11] 4,366,812
[45] Jan. 4, 1983

[54] ADJUSTABLE DIGITAL AND METACARPAL SPLINT APPARATUS

[75] Inventor: Roy Nuzzo, Westfield, N.J.
[73] Assignee: Delos, Inc., Metuchen, N.J.
[21] Appl. No.: 266,796
[22] Filed: May 26, 1981
[51] Int. Cl.³ .............................................. A61F 5/10
[52] U.S. Cl. ................................. 128/77; 128/87 A
[58] Field of Search ................. 128/77, 87 A, 87 R, 128/83, 165

[56] References Cited

U.S. PATENT DOCUMENTS 2,863,449 12/1958 Spencer ............................ 128/87 A

FOREIGN PATENT DOCUMENTS 270341 9/1913 Fed. Rep. of Germany ... 128/87 A
306715 4/1917 Fed. Rep. of Germany ........ 128/77
312103 10/1917 Fed. Rep. of Germany ........ 128/77

OTHER PUBLICATIONS

"Burnham Finger Splint", Richards Mfg. Co., Journal Bone and Joint Surgery, vol. 46, No. 3, Apr. 1964, p. 66.

Primary Examiner—John D. Yasko
Attorney, Agent, or Firm—Steinberg & Raskin

[57] ABSTRACT

Digital and metacarpal splint apparatus wherein an elongate splint member is adjustably positionable into anatomical alignment with any one of the fingers of the hand. The apparatus comprises an elongate splint member and apparatus for mounting the splint member to the body for pivotal movement about an axis which passes through an end region of the splint member and for locking the splint member into a selected position.

12 Claims, 7 Drawing Figures

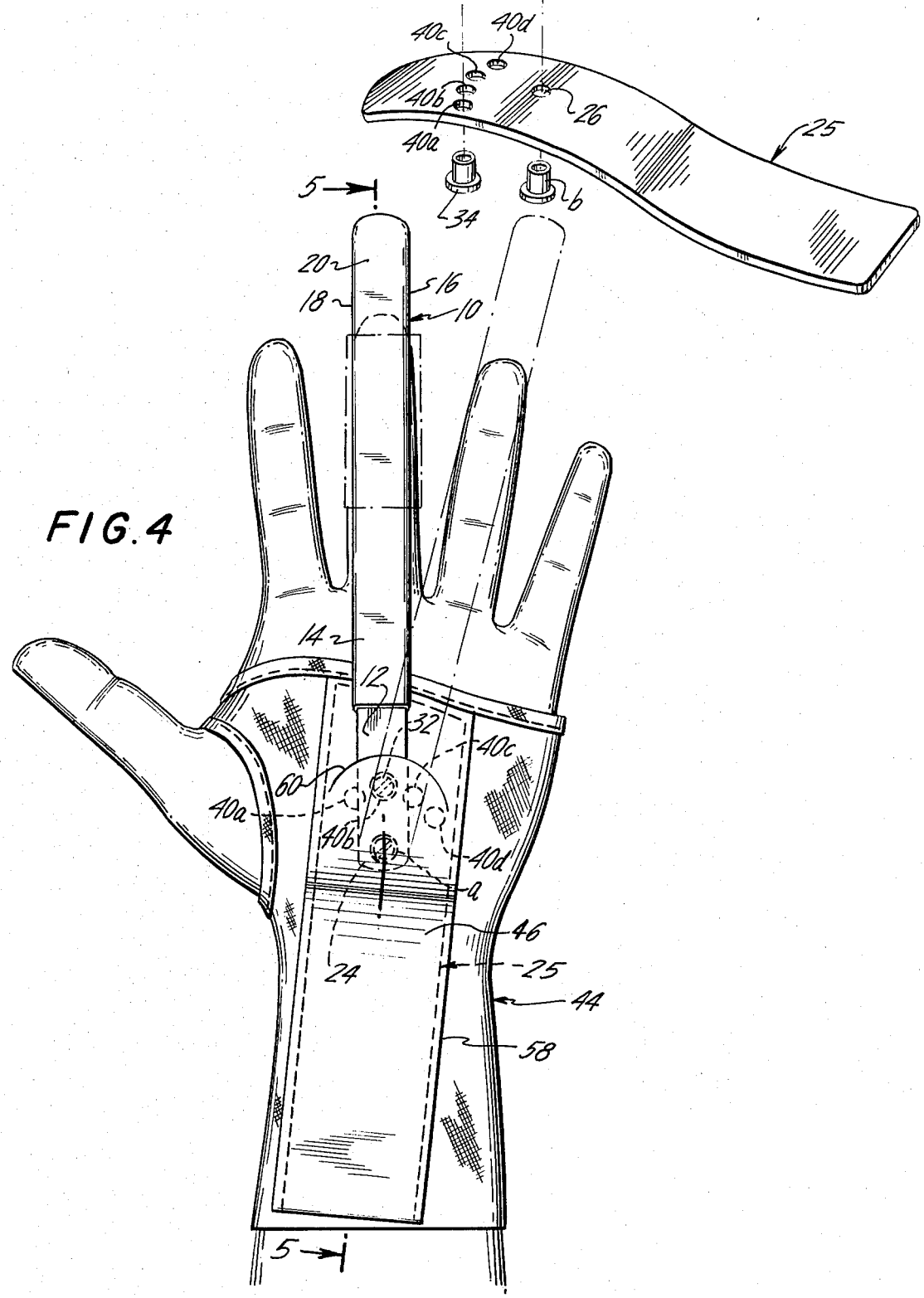

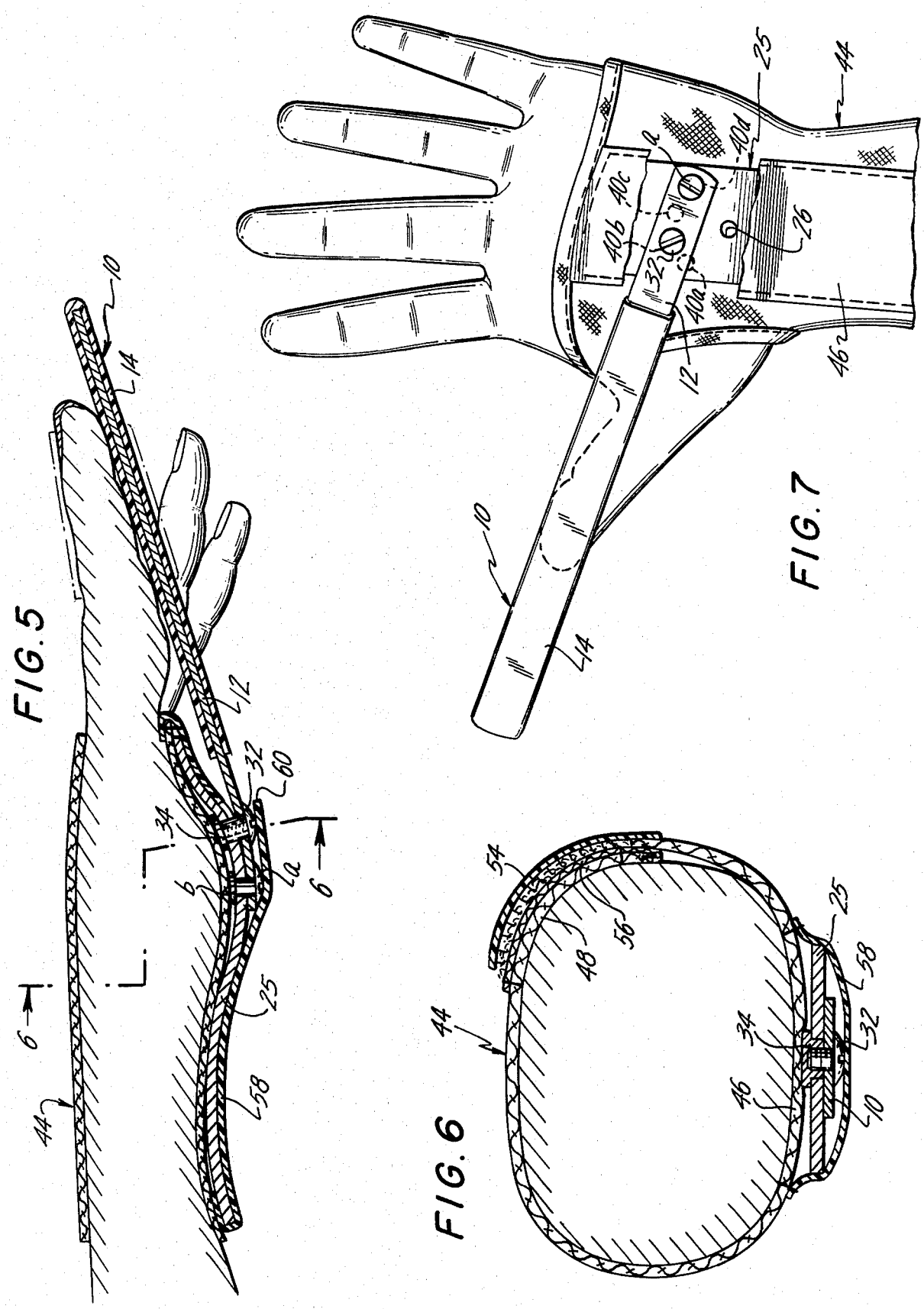

ADJUSTABLE DIGITAL AND METACARPAL SPLINT APPARATUS

BACKGROUND OF THE INVENTION

This invention relates generally to splint apparatus and, more particularly, to digital and metacarpal splint apparatus.

Certain hand and finger injuries are presently treated by applying a splint to the injured finger. In order to provide the necessary rigidity for the splint, the conventional technique in general use today comprises positioning an elongate finger splint having a typical length of about one foot adjacent to the injured finger so that a portion thereof extends adjacent to the hand and forearm region. A plastic cast is then applied over the forearm region so that the splint is held in a rigid manner. The splint is then tightly taped to the finger to immobilize the same.

The conventional procedure summarized above is not entirely satisfactory for several reasons. Firstly, the casting procedure is quite time consuming, often requiring about 45 minutes or more. Secondly, the casting is usually necessarily performed only a short time after the injury occurs so that the forearm region over which the cast is applied is still in a swollen condition. Since, however, the swelling tends to decrease over a period of one or two days, the cast generally becomes loose resulting in the splint not being held in a sufficiently rigid manner to assure proper anatomical alignment with the finger. This of course necessitates a recast operation which requires a revisit to the surgeon. Conversely if the cast is applied to the forearm before it has become completely swollen, the fit will become too tight and possibly necessitate removal thereof with subsequent recasting. Furthermore, it is often difficult to obtain an accurate X-ray of the hand due to the presence of the cast.

SUMMARY OF THE INVENTION

Accordingly, one object of the present invention is to provide new and improved digital and metacarpal splint apparatus which overcome the drawbacks mentioned hereinabove.

More particularly, one object of the present invention is to provide new and improved finger splint apparatus which can be applied in a minimum amount of time.

Another object of the present invention is to provide new and improved finger splint apparatus which can be easily adjusted to compensate for swelling in the region of the arm adjacent to the hand.

A further object of the present invention is to provide new and improved finger splint apparatus wherein the same apparatus can be easily adjusted to provide anatomical alignment with any of the fingers of the hand.

Still another object of the present invention is to provide new and improved finger apparatus which will not prevent an accurate X-ray from being obtained.

Yet another object of the present invention is to provide new and improved finger splint apparatus which is relatively economical in manufacture.

Briefly, in accordance with the present invention, these and other objects are attained by providing a digital and metacarpal splint apparatus wherein an elongate finger splint member can be adjustably positioned so as to be anatomically alignable with any one of the five fingers of the hand. An elongate splint member is adapted so that is can be mounted with respect to the hand for pivotal movement about an axis which passes through an end portion of the splint member and such that the latter can be locked in a selected position in anatomical alignment with a selected one of the fingers.

In a preferred embodiment illustrated herein, the splint apparatus includes an elongate splint member having an end portion, an elongate metallic plate member configured so as to substantially correspond to the contour of a region extending substantially at least between the wrist and palm of the hand, the plate member having a pivot opening formed therein at a location such that when the plate member is mounted over the region extending substantially at least between the wrist and palm, the pivot opening is positioned over an area substantially proximate to the region of the wrist and palm. The end portion of the splint member has a corresponding pivot opening formed therein which is alignable with the plate pivot opening. A pivot member is received within the aligned pivot openings so that the splint member is pivotally mounted on the plate member about an axis which passes through the pivot openings.

In this connection, use is made of the anatomical fact that when flexed, fingers converge toward a small area which is substantially proximate to the region of the wrist and palm as more fully explained hereinbelow.

Apparatus for locking the splint member in a particular position in anatomical alignment with a desired finger are also provided. In a preferred embodiment four locking openings are formed through the plate member in an arcuate configuration and the splint member itself is formed with a corresponding locking opening therethrough which will become aligned with a respective one of the four plate locking openings when the splint member is pivotally attached to the plate member and pivoted into anatomical alignment with a desired respective finger to be set whereupon a locking member can be inserted through the aligned locking openings to lock the splint member in place.

A gauntlet is provided formed of a sheet of elastic fabric material and is adapted to wrap around the hand-forearm region so that a portion thereof overlies the region extending between at least the wrist and palm. A pouch is appropriately provided on the gauntlet in which the plate member is situated to mount the same over the region extending at least between the wrist and palm. Velcro fasteners may be provided on edge regions of the gauntlet so that the latter can be fitted over the hand-forearm region with appropriate tension being applied.

In use, the gauntlet having the plate member situated therein is fitted over the hand-forearm region so that the plate is mounted as described above with the splint member pivotally attached thereto. The splint member is pivoted until it is anatomically aligned with the desired finger to be set whereupon the splint member is locked in the selected position. The position of the splint member will be securely maintained by the plate member which is appropriately configured to conform to the anatomical contour of the region extending between the wrist and the palm and which further serves to immobilize this region of the body. Increases and decreases in swelling in the area over which the gauntlet is fitted can be easily compensated through suitably adjusting the Velcro fasteners provided at the edge regions of the gauntlet. The finger to be set is appropriately secured to the splint member.

The finger splint member is preferably tapered in order to provide greatest strength in the area where it is most required, namely proximally, and can be sufficiently long to enable traction to be applied.

DESCRIPTION OF THE DRAWINGS

A more complete appreciation of the present invention and many of the attendant advantages thereof will be readily appreciated as the same becomes better understood by reference to the following detailed description when considered in connection with the accompanying drawings in which:

FIG. 3 is an exploded view in perspective of the finger splint and plate members comprising components of the present invention and illustrating threaded locking and pivot members used in connection with pivotally mounting and locking the splint member in a selected position;

FIG. 4 is a view of the splint apparatus of the present invention in use; i.e., fitted on the hand of a patient;

FIG. 5 is a sectional view taken along line 5—5 of FIG. 4;

FIG. 6 is a sectional view taken along line 6—6 of FIG. 5; and

FIG. 7 is a view similar to FIG. 4 illustrating the splint member in anatomical alignment with the thumb.

DESCRIPTION OF THE PREFERRED EMBODIMENTS

Figure 1:
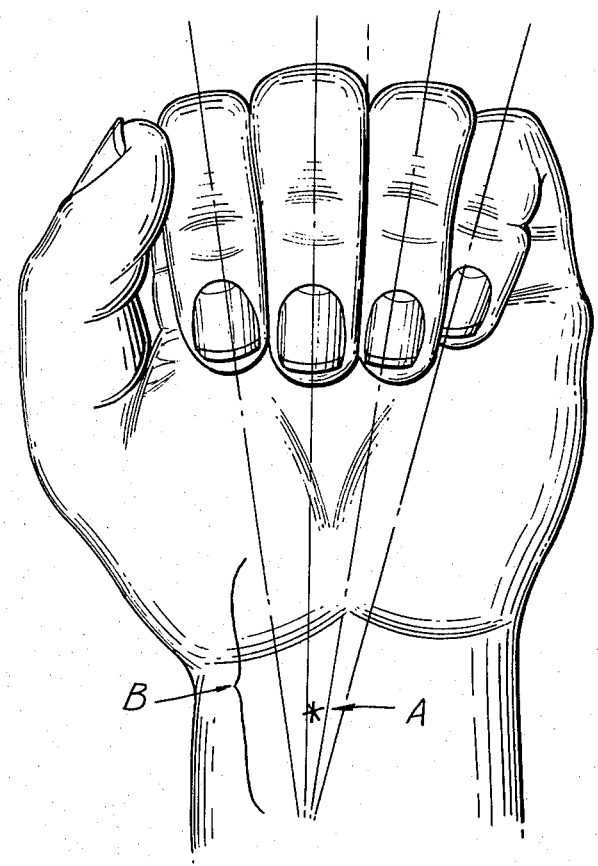
FIG. 1 is a view of the hand with the fingers flexed illustrating the manner in which the same coverage toward an area substantially proximate to the region of the wrist and palm.
Figure 2:
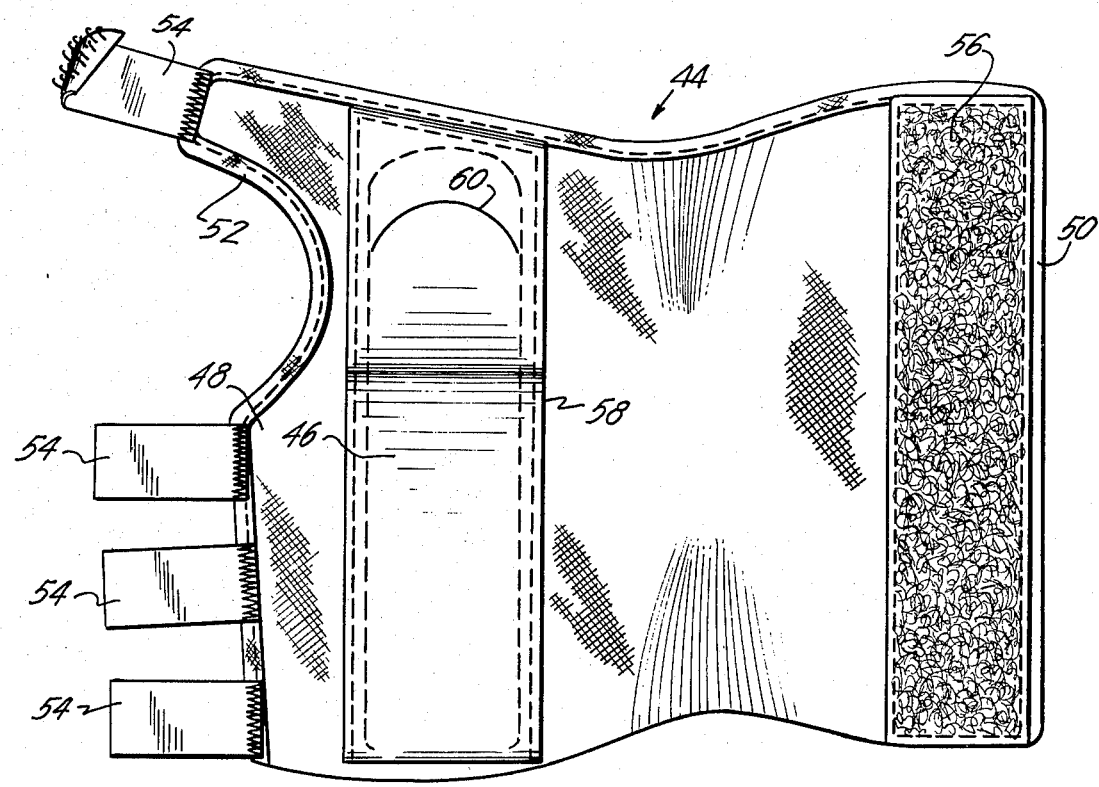
FIG. 2 is a view of a gauntlet member comprising one component of the present invention illustrating the same in its unfolded form.

Referring now to the drawings wherein like reference characters designate identical or corresponding parts throughout the several views, FIG. 1 illustrates the anatomical principle employed by the present invention. Thus, it is seen in FIG. 1 that when flexed, the fingers (other than the thumb) converge toward an area, designated A, which is substantially proximate to the region of the wrist and palm, designated B. This anatomical fact has been utilized to provide digital and metacarpal splint apparatus wherein a splint member is pivotally mounted such that its position can be adjusted into anatomical alignment with any one of the fingers. The present invention incorporates this principle and, together with certain other features, provides apparatus which satisfy all of the objects noted above.

Referring generally to FIGS. 2-6, the splint apparatus of the present invention includes a bone splint in the form of an elongate splint member 10 defined by a plate 12 formed of heavy duty aluminum or the like so as to be sufficiently malleable for fine contouring to the finger and an outer padding 14 covering the plate 12 formed of a closed cell material so as to be water impermeable. The splint member 10 should be sufficiently long so as to allow traction to be applied to the finger, such as by pin or tape or the like, or may be trimmed if no traction is to be applied.

The side edges 16 and 18 of splint member 10 preferably slightly converge towards each other in an outward direction so that the splint member tapers towards its outer end portion 20. This construction has been found advantageous in that it provides the splint member with greatest strength at proximal areas where it is most required.

As best seen in FIG. 3, a pivot opening 22 is formed through the inner end portion 24 of splint member 10.

The splint apparatus further includes a palm plate in the form of metallic plate member 25 formed of heavy duty aluminum or the like which is configured so as to substantially correspond to the contour of a region extending at least between the wrist and the palm as best seen in FIG. 5 so as to be mountable over this region during use as described below.

A pivot opening 26 is formed in plate member 25 at a location such that when the plate member is mounted over the region extending at least between the wrist and the palm, the pivot opening will be positioned over an area substantially proximate to the region of the wrist and palm. Such region substantially corresponds to that designated A in FIG. 1 and is substantially within the region towards which the flexed fingers of the hand converge as described above.

The pivot opening 26 in plate member 25 and pivot opening 22 in splint member 10 are appropriately arranged so that a pivot member can be inserted into the aligned pivot openings 22 and 26. In the illustrated embodiment, the pivot member comprises a threaded member a and a bushing b connectable thereto. Thus, the pivot openings 22 and 26 in the splint and plate members along with the pivot members a, b comprise a pivot device. The plate member is preferably shaped in a manner such that the inner end portion 24 of splint member 10 extends substantially tangentially from the upper surface of the plate member 25 in the area of opening 26 to facilitate pivotal movement of the splint member with respect to the plate member.

In the manner described above, the splint member 10 is mounted on the plate member 25 for pivotal movement about an axis which passes through the pivot opening 26 and it is seen that when the plate member 25 is mounted on the hand in a manner such that the opening 26 is located over the region A of the wrist and palm, that the splint member 10 can be pivoted into substantial anatomical alignment with any of the fingers (except the thumb).

The apparatus is further provided with means in the form of a splint fastener for locking the splint member 10 in a selected position so as to be in alignment with one of the fingers. In a preferred embodiment, the splint fastener comprises four locking openings 40a, 40b, 40c and 40d formed through plate member 25 which together describe an arcuate locus having the pivot opening 26 as its center of curvature. The splint fastener also includes a locking opening 30 formed through the splint member at a spacing from pivot opening 22 which is equal to the radius of curvature of the arcuate locus described by locking openings 40 so that as the splint member is pivoted as described above, splint locking opening 30 will be alignable with any of the four plate locking openings 40. Further, each plate locking opening 40 is situated such that when the splint locking opening 30 is aligned therewith, the splint member 10 will be in anatomical alignment with a respective one of the four fingers. For example, referring to FIG. 4, when the splint locking opening is aligned with plate locking opening 40b, the splint member 10 is anatomically aligned with the middle finger 28.

A locking member, such as a threaded member 32 and associated bushing 34, is adapted to be inserted through a selected plate locking opening 40 and the aligned splint locking opening 30 and, as such, also constitutes a component of the splint fastener. Thus, it will be noted that the pivot device 22, 26, a, b is in a first position that is spaced from a second position where the splint fastener 40a-40d, 30, 32, 34 is located.

Thus, in order to lock the splint member 10 in a position wherein it is anatomically aligned with a finger to be set, the splint member is pivoted until the splint locking opening 30 is aligned with the proper plate locking opening 40, e.g., opening 40b in FIG. 4, whereupon the threaded member 32 is passed through the aligned openings and bushing 34 attached thereto as seen in FIGS. 5 and 6. It is therefore seen that the splint member is connected to the plate member 25 at two distinct points, namely at the first position where the pivot device is located and at the second position where the splint fastener is located. The splint member and locking plate will thus be in an immobile assembled position relative to one another.

In order to mount the plate member 25 in the position illustrated in FIGS. 4 and 5 and such that the opening 26 is positioned over an area substantially proximate to the region A of the wrist and palm, a gauntlet member 44 formed of an elastic material such as the type used in Ace bandages is provided. The gauntlet member 44 is adapted to be fitted over the hand-forearm region in a manner such that a portion 46 thereof will overlie a region extending at least between the wrist and palm. In the illustrated embodiment, the gauntlet member 44 comprises a sheet of elastic material adapted to be wrapped around the hand-forearm region as best seen in FIGS. 4-6. The sheet of elastic fabric material has a pair of edge regions 48 and 50 (FIGS. 2 and 6) which will be situated in opposed relationship to each other when the elastic sheet of the gauntlet member is wrapped around the hand. The edge region 48 is formed with a cutout 52 to provide an opening through which the thumb can extend. Further, hook and loop fasteners 54 and 56 are provided on edge regions 48 and 50, respectively, for reasons which will become clear hereinbelow.

In order to attach the plate member 25 to the inner portion 46 of gauntlet member 44 so that the plate member can be mounted over the area B, a sheet 58 of heavy material, such as leather or the like, is sewn to the gauntlet member 44 over the inner portion 46 around its periphery so as to define a pouch therewithin. An arcuate cut 60 is formed in sheet 58. Before completion of the sewing of the sheet 58 to the gauntlet member 44, the plate member 25 is situated in the pouch defined therewithin in the manner illustrated in FIGS. 5 and 6. The pouch defined by the sheet 58 is appropriately configured so as to hold the member 25 securely therein. The materials from which the gauntlet member 44 and sheet 58 are formed are sufficiently heavy to hold the plate member 25 secure against movement. It is noted in this connection that plate member 25 and gauntlet member 44 can effectively function as a wrist splint apparatus in combination with the other advantageous functions of the invention.

Having described the components of the illustrated embodiment of the present invention, the application thereof to a patient will now be described. The gauntlet member 44 with the plate member 25 attached thereto as described above is wrapped around the hand-forearm region so that the plate member is mounted on and overlies at least the region B extending between the wrist and palm and by virtue of its configuration conforms to the contour thereof as seen in FIG. 5. The edge region 48 and 50 of the gauntlet member are connected to each other by the hook and loop fasteners 52 and 56 in a manner so that the elastic sheet material of gauntlet member 44 is stretched to some extent to both substantially fix the plate member in place and to achieve the best fit under the particular circumstances of the injury and skin condition. In this connection, it is noted that as swelling decreases or increases, it is a simple matter to adjust the tension of the gauntlet member by suitably resetting of one or more of the fasteners 54.

The splint member 10 has preferably been previously pivotally attached to the plate member 25 with the pivot member a and b extending through aligned pivot openings 22 and opening 26. It is of course understood that the splint member 10 can be mounted to the plate member 25 subsequent to the gauntlet member 44 being fitted over the hand.

The splint member 10 is then pivotally adjusted into anatomical alignment with the finger desired to be set, such as the middle finger shown in FIG. 4, whereupon the locking member 32 is inserted through the splint locking opening 30 and particular plate locking opening aligned therewith, and fastener 34 is tightened to lock the splint member in the selected position. As seen in FIG. 4, it is an easy matter to pivotally adjust the position of the splint member 10 such as from the position illustrated in phantom to the position in solid lines. Since the axis about which the splint member 10 rotates passes through an area substantially proximate to the region A of the wrist and palm towards which the fingers converge, the splint member 10 can be brought into proper anatomical alignment with any selected one of the fingers (except the thumb) in the manner described above.

The illustrated apparatus is further provided with a feature whereby the splint member can be fixed to the plate member so as to align with the thumb when necessary. Thus, referring to FIG. 7, the plate locking openings 40b and 40d can be located such that firstly, the spacing between openings 40b and 40d is equal to the spacing between each plate locking opening and the plate pivot opening 26, i.e., so that pivot opening 26 and locking openings 40b and 40d form an equilateral triangle. It will be readily understood that the splint member can thus be positioned and connected to the plate member with the splint member openings 22 and 30 aligned over plate locking openings 40d and 40b, respectively. Secondly, the locking openings 40b and 40d are located such that when the splint member is fixed to the plate member with splint locking opening 30 aligned with plate locking opening 40b and splint pivot opening 22 aligned with plate locking opening 40d, the splint member extends in anatomical alignment with the thumb as seen in FIG. 7. The locking and pivot members of course pass through the pair of aligned openings.

It is seen from the above that the present invention provides significant advantages. Thus, the rigidity of the splint member will be assured regardless of the reduction or increase of swelling through the appropriate adjustment of the gauntlet 44 as described above. The time required to apply the splint apparatus is as low as 25 to 40 seconds as compared to about 45 minutes required for conventional techniques. Accurate X-rays can be taken while the patient is wearing the splint apparatus and clearly the cost of manufacture is relatively low.

The particular configuration of the splint members can of course vary and extra heavy duty splints may be utilized to accommodate particular circumstances. The splint may be adapted for use in connection with traction for noncircumferencial immobilization of the fingers when only a mild swelling is anticipated and for maintenance of reduction of some unstable fractures. Accessories for skin traction and for periostal traction can be incorporated.

Obviously, numerous modifications and variations of the present invention are possible in the light of the above teachings. It is therefore to be understood that within the scope of the claims appended hereto, the invention may be practiced otherwise than as specifically disclosed herein.

What is claimed is:

1. An adjustable digital splint for a hand, said splint comprising
   an elongate bone splint,
   a plate member configured to substantially correspond to, and sized to overlie, the contour of a portion of a user's hand on the palm side thereof;
   connector structure that cooperates with said bone splint and with said plate member for holding said bone splint and plate member in immobile assembled position relative one to the other, said connector structure comprising
   a pivot device that couples said bone splint to said plate member at a first position, said pivot device permitting pivotal movement of said bone splint relative to said plate member about an axis to select the final use position of said bone splint,
   a splint fastener that couples said bone splint to said plate member at a second position, said splint fastener holding said bone splint in the selected pivot position relative to said axis, the first and second connection positions of said bone splint and said plate member being spaced one from the other, the first and second spaced positions of said bone splint and plate member connections maintaining said bone splint and plate member in the immobile nonpivoting assembled position one with the other through use of said splint fastener even if the pivot device connection is a loose connection, and
   means for mounting said plate member over the hand of a user on the palm side thereof.

2. The combination of claim 1 wherein said plate member is configured to substantially correspond to, and sized to overlie, the contour of a user3 s hand between the wrist and palm thereof.

3. The combination of claim 1 wherein said pivot device permits pivotal movement of said bone splint relative to said plate member about an axis located substantially adjacent the heel of a user's hand.

4. The combination of claim 1 wherein sad plate member mounting means comprise a sleeve defined at least in part by an elastic fabric material, said sleeve including a pouch fixed to said sleeve on the palm side thereof, said plate member being received in said pouch for connecting said plate member to said sleeve, and said sleeve being sized to cover both at least a portion of a user's hand and wrist when said splint is installed on the user's hand for enhancing stability of said bone splint and plate member assembly on the user's hand.

5. The combination of claim 4, said plate members and said connector structure being substantially completely enclosed within said pouch, said bone splint thereby being connected to said plate member inside of said pouch and extending outwardly through an opening in said pouch.

6. The combination of claim 4, said sleeve comprising
   a gauntlet having opposite side edges disposed generally parallel to the longitudinal axis of a user's hand and arm when said splint is installed, and
   gauntlet fasteners connected to said opposed side edges, said gauntlet fasteners being adapted to hold said sleeve tight about a user's hand and wrist when said splint is installed.

7. The combination of claim 6, said gauntlet fasteners comprising
   hook and loop fasteners, said hook and loop fasteners being partially carried on each of said opposed side edges, said hook and loop fasteners permitting said sleeve to be tightened or loosened as desired depending on the swelling or lack thereof of the user's hand.

8. The combination of claim 1, said connector structure being adapted to hold a single bond splint in any one of four positions, each position serving the digital bones of different one of a hand's four fingers.

9. The combination of claim 1, said splint fastener comprising
   a plurality of locking openings formed through said plate member and a locking opening formed through said bone splint, said plate member locking openings being located such that said splint locking opening is selectively alignable with each of said plate member locking openings to position said bone splint in anatomical alignment with a selected finger upon pivoting said bone splint about said axis.

10. The combination of claim 9, wherein said plurality of locking openings include four locking openings in said palm plate that define a generally arcuate locus.

11. The combination of claim 9, said connector structure being adapted to hold said single bone splint in a position that serves the digital bones of a hand's thumb.

12. The combination of claim 10 wherein the spacing between a selected two of said plate member locking openings is substantially equal to the spacing between each plate member locking opening and said first position so that said selected two plate member locking openings and said first position form an equilateral triangle and wherein said selected two plate member locking openings are located such that said bone splint is coupleable to said selected locking openings in immobile assembled position relative one to the other and so that said splint member extends in anatomical alignment with the thumb of the hand of the user.

* * * * *